United States Patent [19]

Imada et al.

[11] Patent Number: 4,504,655

[45] Date of Patent: Mar. 12, 1985

[54] SUBSTANCES POTENTIATING THE ACTIVITY OF ANTIBIOTICS AND THEIR PRODUCTION

[75] Inventors: Akira Imada, Hyogo; Kazuhiko Kintaka; Susumu Shinagawa, both of Osaka, all of Japan

[73] Assignee: Takeda Chemical Industries, Ltd., Osaka, Japan

[21] Appl. No.: 463,542

[22] Filed: Feb. 3, 1983

Related U.S. Application Data

[63] Continuation-in-part of Ser. No. 448,917, Dec. 9, 1982, abandoned.

[30] Foreign Application Priority Data

Jul. 7, 1981 [JP] Japan .................................. 56-106554
Feb. 15, 1982 [JP] Japan .................................. 57-23099
Dec. 24, 1982 [JP] Japan .................................. 57-232055

[51] Int. Cl.³ .................... C08B 37/00; A01N 31/00; A61K 31/71
[52] U.S. Cl. ................................................. 536/18.7
[58] Field of Search ................. 536/18.7, 23; 424/117, 424/181, 180

[56] References Cited

U.S. PATENT DOCUMENTS 4,225,586 9/1980 Imada et al. ................... 424/117
4,229,436 10/1980 Imada et al. ................... 424/117

OTHER PUBLICATIONS

Imada et al., Sulfazecin and Isosulfazecin ..., Nature 289, 590–591, (1981).
Kintaka et al., Isosulfazecin, A new B-lactam Antibiotic, Produced by ..., Pseudomonad, J. Antibiotics, 34 (9), 1081–1089, (1981).

Primary Examiner—Delbert R. Phillips
Assistant Examiner—Charles H. Thieman
Attorney, Agent, or Firm—Wenderoth, Lind & Ponack

[57] ABSTRACT

Novel compound having the formula and salts thereof:

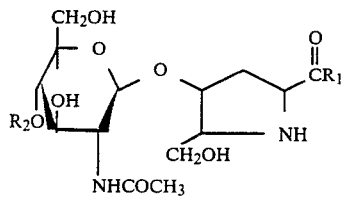

wherein $R_1$ is $NHCH_2CH_2SO_3H$ or OH and $R_2$ is $SO_3H$ or H, which potentiate the antibacterial activity of β-lactam antibiotics and can be used for the treatment of infectious diseases caused by bacteria in mammals or domestic fowls, etc.

2 Claims, 7 Drawing Figures

SUBSTANCES POTENTIATING THE ACTIVITY OF ANTIBIOTICS AND THEIR PRODUCTION

This application is a continuation-in-part of International Application No. PCT/JP 82/00255 designating the U.S., filed July 7, 1982 in Japan, which entered the national stage in the U.S. as Ser. No. 448,917 filed Dec. 9, 1982, now abandoned.

TECHNICAL FIELD

This invention relates to novel substances which potentiate the activity of antibiotics, salts thereof, and their production.

Background Art

Until now, the protein SP127 has been known as a substance which potentiates the activity of antibiotics (M. Kikuchi et al.; The Journal of Antibiotics 30, 209–214, 1977), and it potentiates the antibacterial activity of macrolide antibiotics (ibid. 30, 215–220, 1977). On the other hand, clavulanic acid is known as a substance which prevents inactivation of β-lactam antibiotics by β-lactamases and synergistically potentiates their activity against β-lactamase producing bacteria [D. A. Leigh et al., Journal of Antimicrobial Chemotherapy, (1981)7, 229–236].

Disclosure of the Invention

The present inventors isolated from soil samples a large number of microorganisms for the purpose of developing new antibiotic substances, and searched for antibiotics in the metabolites elaborated by these microorganisms. This exploration led them to the finding that certain strains among these isolates produce novel substances which potentiate antibacterial activity, that the strains belong to the genus Pseudomonas, and that the substances capable of potentiating the antibacterial activity of β-lactam antibiotics against gram-negative bacteria can be caused to accumulate in a culture medium by growing such a strain of microorganism therein. The present inventors isolated the substances, studied their physical, chemical and biological characteristics and, based on these characteristics, confirmed that these substances which potentiate antibacterial activity are novel active substances. Furthermore, it has also been found that the partial hydrolyzates of the above substances potentiate the activity of antibiotics.

It is the principal object of the present invention to provide a compound, inclusive of salts thereof, which has the formula (I):

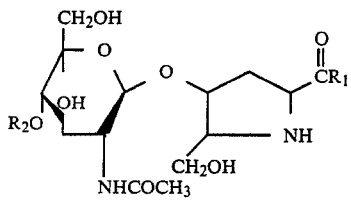

wherein $R_1$ is $NHCH_2CH_2SO_3H$ or OH and $R_2$ is $SO_3H$ or H.

Another object is to provide a method for producing a compound, which has the formula (II):

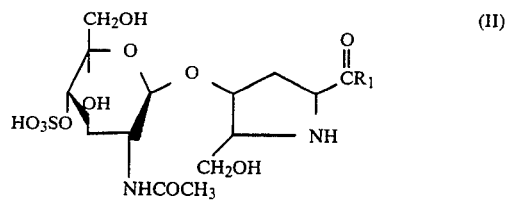

wherein $R_1$ is $NHCH_2CH_2SO_3H$ or OH, by means of microbial fermentation using a microorganism which belongs to the genus Pseudomonas.

A further object is to provide a method for producing a compound, inclusive of salts thereof, which has the formula (III):

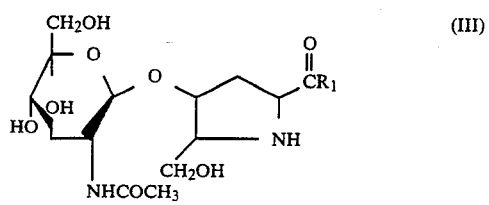

wherein $R_1$ is $NHCH_2CH_2SO_3H$ or OH, which comprises subjecting a compound of the formula (IV), inclusive of salts thereof:

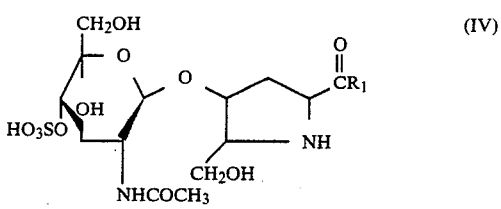

wherein $R_1$ is $NHCH_2CH_2SO_3H$ or OH, to desulfation.

It should first be noted that in this specification four compounds represented by the formula (I) will sometimes be referred to briefly as $F_2$, $F_3$, $F_4$ or $F_5$ as shown in the following Table.

| Abbreviations of compounds | $R_1$ | $R_2$ |
|---|---|---|
| F2 | $NHCH_2CH_2SO_3H$ | $SO_3H$ |
| F3 | OH | $SO_3H$ |
| F4 | $NHCH_2CH_2SO_3H$ | H |
| F5 | OH | H |

A compound of the formula (II), F2 and F3 inclusive, of the present invention may be produced by means of microbial fermentation. The F2- and F3-producing strain may be any species of microorganism which belongs to the genus Pseudomonas and is capable of elaborating a compound of the formula (II). For example, *Pseudomonas acidophila* G-6302 and *Pseudomonas mesoacidophila* SB-72310 may be mentioned.

The strain G-6302 and the strain SB-72310 have been deposited at the Fermentation Research Institute, the Agency of Industrial Science and Technology (FRI, 1-3, Yatabecho higashi 1-chome, Tsukuba-gun, Ibaraki, Japan), Institute for Fermentation, Osaka (IFO, 17-85, Jusohonmachi 2-chome, Yodogawa-ku, Osaka, Japan) and The American Type Culture Collection (ATCC, 12301 Parklawn Drive, Rockville, Md. 20852 U.S.A.), respectively, as follows:

|  |  | FRI | IFO | ATCC |
|---|---|---|---|---|
| The strain G-6302 | Deposit number | FERM-P No. 4344 | IFO 13774 | ATCC 31363 |
|  | Date of deposit | December 20, 1977 | December 20, 1977 | December 28, 1977 |
| The strain SB-72310 | Deposit number | FERM-P No. 4653 | IFO 13884 | ATCC 31433 |
|  | Date of deposit | September 13, 1978 | September 13, 1978 | September 25, 1978 |

The morphological characteristics of the strain G-6302 are described in Japanese Patent Application Laid-open No. 163501/1979 and U.S. Pat. No. 4,229,436 (Patented on Oct. 21, 1980), and those of the strain SB-72310 in Japanese Patent Application Laid-open No. 49394/1980 and U.S. Pat. No. 4,225,586 (Patented on Sept. 30, 1980).

The strains belonging to the genus Pseudomonas which are employed in accordance with this invention are generally liable to vary their characteristics and behaviors and tend to undergo mutation when exposed to ultraviolet light, X-rays, chemical mutagens and other artificial agents. However, even such mutants or variants can be employed, but only if they are able to elaborate a compound of the formula (II).

In cultivating the above strains, mutants and variants, there are employed such assimilable carbon sources as glucose, sucrose, maltose, spent molasses, glycerol, oils (e.g. soybean oil, olive oil, etc.), organic acids (e.g. citric acid, succinic acid, gluconic acid, etc.). The nitrogen sources that may be employed include various organic and inorganic nitrogen compounds such as soybean meal, cottonseed meal, corn steep liquor, dried yeast, yeast extract, meat extract, peptone, urea, ammonium sulfate, ammonium nitrate, ammonium chloride, ammonium phosphate, etc. There are also employed such inorganic salts as are commonly used in the cultivation of bacteria, such as sodium chloride, calcium chloride, calcium carbonate, magnesium sulfate, monopotassium phosphate, disodium phosphate, etc. It was found that sulfur compounds which the strains can utilize, i.e. inorganic sulfur compounds such as sodium sulfate, sodium thiosulfate, etc. and organic sulfur compounds such as cystine, cysteine, methionine, etc. lead to an increased yield of a compound of the formula (II). Particularly preferred are cysteine and sodium thiosulfate. The concentration of such sulfur compounds is 0.01 to 1.0 w/v % and preferably 0.02 to 0.5 w/v %. The addition of a sulfur compound to the medium results in an increased yield of a compound of the formula (II) and is therefore very advantageous in commercial-scale production.

If necessary, there are also incorporated in the culture medium heavy metal compounds such as ferrous sulfate, tin sulfate, etc. and vitamins such as vitamin $B_1$, biotin, etc. It is also possible or advantageous to add an antifoam or/and a surfactant, such as silicone oil, polyalkylene glycol ether, etc. In addition, organic or/and inorganic materials that will promote production of a compound of the formula (II) may also be incorporated in suitable amounts.

The cultivation can be carried out either in solid medium or in liquid medium by a conventional antibiotics production method. While the cultivation in liquid medium may be conducted under stationary conditions or with stirring, shaking or aeration, spinner culture under aeration is especially preferred. The cultivation is performed preferably at a temperature within the range of about 15° C.–35° C., at a pH of the medium within the range of about 4–8, generally for about 8–168 hours, preferably for 24–144 hours.

The thus-produced compound of the formula (II), which is present for the most part in the culture broth filtrate, is advantageously isolated and purified from the supernatant following separation of the culture broth into a supernatant and bacterial cells by centrifugation or filtration. It is also possible to isolate and purify a compound of the formula (II) directly from the culture broth.

The potency of the compound of the formula (II) can be determined, for instance, by the cup method or paper disc method using bouillon agar containing 0.05 μg/ml of cefmenoxime with *Escherichia coli* IFO 12734 as the test organism.

The compound of the formula (II) can be harvested by any means commonly used for harvesting metabolites produced by microorganisms. Thus, for example, bacterial cells are removed by centrifugation and the filtrate is subjected to a common process known for isolation and purification of effective substances. Thus, there are utilized solubility or solubility difference in an adequate solvent, difference in manner or rate of precipitation from a solution, difference in affinity with a variety of adsorbents, ion exchange chromatography with an ion exchanger, concentration under reduced pressure, lyophilization, crystallization, recrystallization, drying and other means, either alone or in combination in an optional order, either singly or repeatedly.

A specific example of recovering the metabolites is given as follows. The culture broth after completion of the cultivation is filtered, the filtrate is passed through an activated carbon column, and the thus-adsorbed compound (II) is eluted with a hydrophilic organic solvent system. The hydrophilic organic solvent system is, for example, a mixed solution composed of water and one or more of lower ketones, such as acetone, methyl ethyl ketone and methyl isobutyl ketone, and lower alcohols, such as methanol, ethanol, isopropanol, propanol and butanol. Since the desired compound is an acidic substance, the ion exchange resin is advantageously a Cl-type one, such as an anion exchange resin (Amberlite IRA-400, 402, Rohm & Haas, USA; Dowex-1, Dow Chemical, USA; Diaion SA-21A, Mitsubishi Chemical, Japan). The thus-adsorbed active substance is eluted with an aqueous solution of sodium chloride, for instance. For desalting, the eluate is again subjected to activated carbon column chromatography. The eluate containing the active substance is concentrated, then acetone or the like is added, and the precipitate is collected by filtration, washed with acetone, ether or the like and dried to give a pale brown powder. For further purification of the powder, column chromatography with QAE Sephadex (Pharmacia, Sweden) is advantageous. Thus, after washing QAE Sephadex A-25 with phosphate buffer (pH 6.6), an aqueous solution of the above powder is passed through the column for adsorption, and the column is washed with M/25 phosphate buffer and then eluted with the same buffer containing 0.5 w/v % of sodium chloride to obtain F3 active fractions. Then the elution is carried out by using the same buffer containing 1.0 w/v % of sodium chloride to obtain F2 active fractions.

The thus obtained F3 active fractions are pooled, adjusted to lower than pH 6 and again passed through an activated carbon column. After washing with water, elution is performed with 50 v/v % methanol-water. The active fractions are concentrated under reduced pressure, and then F3 is obtained in powdery form by lyophilization.

On the other hand, F2 active fractions are pooled, adjusted to lower than pH 3 and again passed through an activated carbon column. After washing, elution is performed with aqueous acetone or 7 v/v % isobutanol-water. The active fractions are concentrated under reduced pressure. Upon addition of acetone, F2 is obtained.

F2 and F3 can form a metal or ammonium salt, respectively. The metal salt is, for example, the sodium, potassium or lithium salt. These salts can be used as pharmaceutical salts.

The physicochemical properties of F2 and F3 are as follows:

The physicochemical properties of the monosodium salt of F2 as obtained in Example 1 are as follows:
1. Melting point: 216°–219° C. (decomposition)
2. Appearance: Colorless crystalline powder
3. Elemental analysis (for the sample dried over phosphorus pentoxide at 40° C. under reduced pressure for 6 hours): C—32.11 (%), H—5.38, N—7.27, S—10.67, Na—3.8.
4. Molecular weight: 605 (calculated as the monosodium salt).
5. Ultraviolet absorption spectrum: End absorption only (no characteristic absorption at wavelength over 210 nm)
6. Infrared absorption spectrum: An absorption spectrum as recorded by the potassium bromide disc method is shown in FIG. 1.
7. Specific rotation: $[\alpha]_D^{26}+6.85°$ (c=0.38, N—CH$_3$COOH) $[\alpha]_D^{26}-7.72°$ (c=0.544, pH 7 phosphate buffer)
8. Nuclear magnetic resonance spectrum (100 MHz, in dimethyl sulfoxide): A—CH$_3$ signal is observed at δ1.84.
9. Solubility: Insoluble in petroleum ether, hexane, diethyl ether, benzene, ethyl acetate and chloroform; sparingly soluble in ethanol, pyridine and acetone; soluble in methanol and dimethyl sulfoxide; readily soluble in water.
10. Color reactions: Positive Greig-Leiback and potassium permanganate reactions; negative ninhydrin, Sakaguchi and Molisch reactions.
11. Stability: Stable in aqueous solution at pH 3–9 against heating at 60° C. for 10 minutes.
12. Acidity/basicity: An acid substance The physicochemical properties of the disodium salt of F2 as obtained in Example 2 are as follows:
1. Melting point: No distinct melting point
2. Appearance: White powder
3. Elemental analysis (for the sample dried over phosphorus pentoxide at 40° C. under reduced pressure for 6 hours): C—31.35 (%), H—5.24, N—6.78, S—10.38, Na—7.1.
4. Molecular weight: 647.6 on the supposition that each molecule contains 2 Na atoms.
5. Ultraviolet absorption spectrum: End absorption only.
6. Infrared absorption spectrum: An absorption spectrum as recorded by the potassium bromide disc method is shown in FIG. 2.
7. Specific rotation: $[\alpha]_D^{26}+5.5°$ (c=0.56, N—CH$_3$COOH)
8. Solubility: Insoluble in petroleum ether, hexane, diethyl ether, benzene, ethyl acetate, chloroform and acetone; sparingly soluble in methanol, ethanol and pyridine; soluble in dimethyl sulfoxide; readily soluble in water.
9. Color reactions: Positive Greig-Leaback and potassium permanganate reactions; negative ninhydrin, Sakaguchi and Molisch reactions.
10. Stabiity: Stable in aqueous solution at pH 3–9 against heating at 60° C. for 10 minutes.

The physico-chemical properties of the monosodium salt of F2 as obtained in Example 3 are as follows:
1. Melting point: 207°–208° C. (decomposition)
2. Appearance: Colorless crystalline powder
3. Elemental analysis (for the sample dried over phosphorus pentoxide at 40° C. under reduced pressure for 6 hours): C—32.59 (%), H—5.22, N—6.93, S—10.14, Na—3.7.
4. Molecular weight: 621.6 (calculated as the monosodium salt).
5. Ultraviolet absorption spectrum: End absorption only (no characteristic absorption at wavelengths over 210 nm)
6. Infrared absorption spectrum: An absorption spectrum as recorded by the potassium bromide disc method is shown in FIG. 3.
7. Specific rotation: $[\alpha]_D^{26}+6.0°$ (c=0.47, N—CH$_3$COOH)
8. Nuclear magnetic resonance spectrum (100 MHz, in dimethyl sulfoxide): A —CH$_3$ signal is observed at δ1.84.
9. Solubility: Insoluble in petroleum ether, hexane, diethyl ether, benzene, ethyl acetate and chloroform; sparingly soluble in ethanol, pyridine and acetone; soluble in methanol and dimethyl sulfoxide; readily soluble in water.
10. Color reactions: Positive Greig-Leaback and potassium permanganate reactions; negative ninhydrin, Sakaguchi and Molisch reactions.
11. Stability: Stable in aqueous solution at pH 3–9 against heating at 60° C. for 10 minutes.
12. Acidity/basicity: An acid substance.

The physico-chemical properties of the disodium salt of F2 as obtained in Example 4 are follows:
1. Melting point: No distinct melting point
2. Appearance: White powder
3. Elemental analysis (for the sample dried over phosphorus pentoxide at 40° C. under reduced pressure for 6 hours): C—30.83 (%), H—5.35, N—6.91, S—9.68, Na—7.3.
4. Molecular weight: 629.9 on the supposition that each molecule contains 2 Na atoms.
5. Ultraviolet absorption spectrum: End absorption only.

6. Infrared absorption spectrum: An absorption spectrum as obtained by the potassium bromide disc method is shown in FIG. 4.
7. Specific rotation: $[\alpha]_D^{26}+6.1°$ (c=0.39, N—CH$_3$COOH)
8. Solubility: Insoluble in petroleum ether, hexane, diethyl ether, benzene, ethyl acetate, chloroform and acetone; sparingly soluble in methanol, ethanol and pyridine; soluble in dimethyl sulfoxide; readily soluble in water.
9. Color reactions: Positive Greig-Leaback and potassium permanganate reactions; negative ninhydrin, Sakaguchi and Molisch reactions.
10. Stability: Stable in aqueous solution at pH 3-9 against heating at 60° C. for 10 minutes.

The physico-chemical properties of F3 monosodium salt as obtained in Example 5 are as follows.
1. Appearance of the substance: White powder
2. Elemental analysis: As dried in vacuo over phosphorus pentoxide at 40° C. for 6 hrs. (%), C—32.08, H—5.33, N—5.17, S—6.28, Na—4.60.
3. Molecular weight: 520±60 as calculated from the sodium content of monosodium salt.
4. Ultraviolet absorption spectrum: End absorptions only (no characteristic at wavelength over 210 nm).
5. Infrared absorption spectrum (FIG. 5): The dominant peaks on the absorption spectrum (KBr disk) are as follows. 3350, 3100(sh), 2950, 1660(sh), 1640, 1560(sh), 1410, 1375, 1320(sh), 1260, 1240, 1110 1070(sh), 1030, 985, 950(sh), 820, 610, 585$^{(cm-1)}$
6. Specific rotation: $[\alpha]_D^{25}-2.8°$ (c=0.5, 0.1M—Na$_2$HPO$_4$)
7. Solubility: Insoluble in petroleum ether, hexane, diethyl ether, benzene, ethyl acetate and chloroform; only sparingly soluble in ethanol, pyridine and acetone; soluble in methanol and dimethyl sulfoxide; and readily soluble in water.
8. Color reactions: Positive Greig-Leaback, ninhydrin and potassium permanganate reactions. Negative ferric chloride-potassium ferricyanide reactions.
9. Stability: Stable in aqueous solution at pH 3 to 9 against heating 60° C. for 10 minutes.

In the present invention, a compound of the formula (III), inclusive of salts thereof, can be produced by subjecting a compound of the formula (IV), inclusive of salts thereof, to desulfation. A conventional method for cleavage of sulfuric ester bond, not to be limited, can be employed in the above reaction. For example, the reaction is conducted by using an acid, especially an inorganic acid such as sulfuric acid or hydrochloric acid, a base such as sodium hydroxide, potassium hydroxide or barium hydroxide, or ion-exchange resin such as Dowex-50 (Dow Chemical, U.S.A.) or Amberlite IR-120 (Rohm and Haas Co., U.S.A.).

In case that an acid is used, the reaction is carried out generally in acid concentration of about 0.005N to 5N, preferably 0.05N to 1N, in the presence of a solvent such as alcohol (e.g. methanol, ethanol, propanol), dioxane, acetic acid, water or a mixture thereof. The reaction is generally performed at about 20° C. to 200° C. for about 30 minutes to 48 hours.

In case that a base is used, the reaction is carried out generally in base concentration of about 0.005N to 5N, preferably 0.05N to 1N, in the presence of alcohol (e.g. methanol, ethanol, propanol), water or a mixture thereof, at about 20° C. to 200° C. for about 30 minutes to 48 hours.

In case that ion-exchange resin is used, the reaction is carried out by using the resin which is suspended in alcohol (e.g. methanol, ethanol, propanol), water or a mixture thereof, at about 30° C. to 200° C. for about 30 minutes to 30 hours.

A compound of the formula (III) can be obtained from the resultant reaction mixture by any means commonly used for isolation and purification of effective substances. Thus, there are utilized ion exchange chromatography with an ion exchanger, adsorption, concentration, crystallization, recrystallization and other means, either singly or repeatedly.

A practical example of the purification process is as follows. The reaction mixture is passed through alkaline ion exchange resin column and then eluted with acetic acid or hydrochloric acid etc.

The fractions, which show positive Greig-Leaback reaction, are pooled and, if necessary, purified by subjecting to gel filtration using Sephadex LH-20 (Pharmacia, Sweden) as carrier and aqueous alcohol as an eluent, respectively.

The biological properties of the compound of the formula (I) are described below. The compound of the formula (I) shows the action which potentiates the antibacterial activity of $\beta$-lactam antibiotics as illustrated from the following data.

(1) The antibiotics-potentiating activity data for F2

It is evident from the data given in Table 1 and Table 2 that F2 exhibits an antibacterial activity against *Escherichia coli* in the copresence of cefmenoxime or mecillinam in a subbactericidal concentration.

Table 1: Cefmenoxime- and mecillinam-potentiating activity data for the F2 sample obtained in Example 1 (test organism: *Escherichia coli* IFO 12734)

TABLE 1

| F2 concentration in test solution** (μg/ml) | Diameter of growth inhibition zone (mm)* | | |
|---|---|---|---|
| | No addition | 0.05 μg/ml cefmenoxime | 0.03 μg/ml mecillinam |
| 0 | <8 | <8 | <8 |
| 1 | <8 | 10 | <8 |
| 5 | <8 | 15 | 10 |
| 25 | <8 | 24 | 18 |
| 125 | <8 | 32 | 24 |
| 1000 | <8 | 40 | 30 |

*The test was performed using a bouillon agar medium containing the antibiotic as specified and a paper disc, 8 mm in diameter.
**A paper disc, 8 mm in diameter, was impregnated with 25 μl of the test solution and placed on the agar medium Table 2: Cefmenoxime- and mecillinam-potentiating activity data for the F2 sample obtained in Example 3 (test organism: *Escherichia coli* IFO 12734)

TABLE 2

| F2 concentration in test solution** (μg/ml) | Diameter of growth inhibition zone (mm)* | | |
|---|---|---|---|
| | No addition | 0.05 μg/ml cefmenoxime | 0.03 μg/ml mecillinam |
| 0 | <8 | <8 | <8 |
| 1 | <8 | 9 | <8 |
| 5 | <8 | 14 | 9 |
| 25 | <8 | 23 | 19 |
| 125 | <8 | 31 | 23 |
| 1000 | <8 | 39 | 29 |

*and**: The same as noted for Table 1.

It is also evident from the data given in Table 3 and Table 4 that F2 is capable of potentiating the antibacterial activity of cefmenoxime and mecillinam against *Proteus mirabilis* ATCC 21100.

Table 3: Cefmenoxime- and mecillinam-potentiating activity data for the F2 sample obtained in Example 1 (test organism: *Proteus mirabilis* ATCC 21100)*

TABLE 3

| F2 concentration in test solution (μg/ml) | Diameter of growth inhibition zone (mm)* | | |
|---|---|---|---|
| | No addition | 0.01 μg/ml cefmenoxime | 0.05 μg/ml mecillinam |
| 0 | <8 | <8 | <8 |
| 1 | <8 | 9 | 9 |
| 5 | <8 | 13 | 11 |
| 25 | <8 | 23 | 19 |
| 125 | <8 | 30 | 26 |
| 1000 | <8 | 38 | 32 |

*The test was performed under the same conditions as noted for Table 1 except for the test organism and the concentration of each coexisting antibiotic.

Table 4: Cefmenoxime- and mecillinam-potentiating activity data for the F2 sample obtained in Example 3 (test organism: *Proteus mirabilis* ATCC 21100)*

TABLE 4

| F2 concentration in test solution (μg/ml) | Diameter of growth inhibition zone (mm)* | | |
|---|---|---|---|
| | No addition | 0.01 μg/ml cefmenoxime | 0.05 μg/ml mecillinam |
| 0 | <8 | <8 | <8 |
| 1 | <8 | 9 | 9 |
| 5 | <8 | 12 | 12 |
| 25 | <8 | 22 | 19 |
| 125 | <8 | 29 | 25 |
| 1000 | <8 | 38 | 32 |

*The test was performed under the same conditions as noted for Table 1 except for the test organism and the concentration of each coexisting antibiotic.

Furthermore, F2 strongly inhibits the growth of *Escherichia coli* in synergy with cephalexin or cefmenoxime. In Table 5 and Table 6, there are shown degrees of growth of *Escherichia coli* under the influence of F2 in the copresence of 5 μg/ml of cephalexin or 1 μg/ml of cefmenoxime.

Table 5: Inhibition of growth of *Escherichia coli* IFO 12734 in the copresence of F2 (obtained in Example 1) and cephalexin or cefmenoxime.

TABLE 5

| Final F2 concentration (μg/ml) | Absorbance at 600 nm | | |
|---|---|---|---|
| | No addition | 5 μg/ml cephalexin | 1 μg/ml cefmenoxime |
| 0 | 2.6 | 2.35 | 1.95 |
| 1 | 2.65 | 1.80 | 0.60 |
| 10 | 2.65 | 1.00 | 0.25 |
| 100 | 2.70 | 0.95 | 0.30 |

To 8 ml of YAB medium (1.75% Difco antibiotic medium No. 3, 0.5% Difco yeast extract) containing 12% (w/v) of sucrose, there were added 1 ml of water, 50 μg/ml cephalexin solution or 10 μg/ml cefmenoxime solution, and the medium was inoculated with 1 ml of a preculture in YAB medium at an early logarithmic growth phase and incubated with shaking at 37° C. for 2 hours. Thereafter, the absorbance of the culture broth was measured at 600 nm using a Shimadzu-Bausch & Lomb Spectronic 20 colorimeter.

Table 6: Inhibition of growth of *Escherichia coli* IFO 12734 in the copresence of F2 (obtained in Example 3) and cephalexin or cefmenoxime*

*The test was performed in the same manner as noted for Table 5.

TABLE 6

| Final F2 concentration (μg/ml) | Absorbance at 600 nm | | |
|---|---|---|---|
| | No addition | 5 μg/ml cephalexin | 1 μg/ml cefmenoxime |
| 0 | 2.4 | 2.15 | 1.90 |
| 1 | 2.45 | 1.75 | 0.55 |
| 10 | 2.50 | 1.90 | 0.25 |
| 100 | 2.55 | 0.75 | 0.25 |

As is evident from Table 5 and Table 6, F2 inhibits the growth of *Escherichia coli* in the presence of cephalexin or cefmenoxime, as evidenced by the decrease in absorbance. Observation of the culture broths under a phase contrast microscope revealed that, when F2 was not added, cells were in the much elongated form under the influence of cephalexin or cefmenoxime but that, when F2 was added, the elongation was inhibited in dependence on the addition level and at the same time partial swelling occurred and bacteriolysis proceeded.

(b) The antibiotics-potentiating activity data for F3

The action of F3, which potentiates the activity of antibiotics, is shown in Table 7 to 9.

Table 7 The action of F3 of Example 5 to potentiate the antibacterial action of cefmenoxime and mecillinam. (Test organism: *Escherichia coli* IFO 12734)

TABLE 7

| Concentration of F3 in test solution** (μg/ml) | Diameter of growth inhibition zone (mm)* | | |
|---|---|---|---|
| | No addition | 0.05 μg/ml of cefmenoxime | 0.03 μg/ml of mecillinam |
| 0 | <8 | <8 | <8 |
| 1 | <8 | 10 | <8 |
| 5 | <8 | 12.5 | <8 |
| 25 | <8 | 15 | 9 |
| 125 | <8 | 26 | 17.5 |
| 1000 | <8 | 38 | 28.5 |

*, **: The test was performed under the similar method as noted for Table 1.

Table 8 The action of F3 of Example 5 to potentiate the antibacterial action of cefmenoxime and mecillinam* (test organism: *Proteus mirabilis* ATCC 21100)

TABLE 8

| Concentration of F3 in test solution (μg/ml) | Diameter of growth inhibition zone (mm)* | | |
|---|---|---|---|
| | No addition | 0.01 μg/ml of cefmenoxime | 0.05 μg/ml of mecillinam |
| 0 | <8 | <8 | <8 |
| 1 | <8 | 9 | <8 |
| 5 | <8 | 12 | 9 |
| 25 | <8 | 21 | 13.5 |
| 125 | <8 | 28.5 | 19 |
| 1000 | <8 | 32.5 | 30 |

*Except for the test organism and the concentration of antibiotics to be potentiated, all other assay conditions are the same as those mentioned for Table 1.

Table 9 Inhibition of growth of *Escherichia coli* IFO 12734: in the co-presence of F3 (Example 5) and cefmenoxime

TABLE 9

| Final concentration of F3 (μg/ml) | Absorbance at 600 nm | |
|---|---|---|
| | No addition | 1 μg/ml of cefmenoxime |
| 0 | 3.7 | 2.9 |
| 1 | 3.7 | 2.2 |
| 10 | 3.7 | 0.6 |
| 100 | 3.7 | 0.6 |

The test was performed in a manner similar to that described for Table 5.

As is evident from Table 9, F3 inhibits the growth of *Escherichia coli* in the presence of cephalexin or cefmenoxime, as evidenced by the decrease in absorbance. Observation of the culture broths under a phase contrast microscope revealed that, when F3 was not added, cells were in the much elongated form under the influence of cephalexin or cefmenoxime but that, when F3 was added, the elongation was inhibited in dependence on the addition level and at the same time partial swelling occurred and bacteriolysis proceeded.

(c) Antibiotics-potentiating activity data for F4

Table 10 Cefmenoxime- and mecillinam-potentiating activity data for the F4 sample obtained in Example 7 (test organism: *Escherichia coli* IFO 12734)

TABLE 10

| F4 concentration in test solution** ($\mu$g/ml) | Diameter of growth inhibition zone (mm)* | | |
|---|---|---|---|
| | No addition | 0.05 $\mu$g/ml cefmenoxime | 0.03 $\mu$g/ml mecillinam |
| 0 | <8 | <8 | <8 |
| 10 | <8 | <8 | <8 |
| 100 | <8 | 15 | 13 |
| 1000 | <8 | 26 | 23 |

*, **: The test was performed under a method similar to that described for Table 1.

Further, the compound of the formula (I) showed a marked antibacterial activity in synergy with cefmenoxime or cephalexin in *Esherichia coli-* or *Proteus mirabilis-* infected mice. Therefore, the compound of the formula (I) can be used in combination with such antibiotics in the treatment of infections diseases caused by the above bacteria in mammals (e.g. mouse, rat, dog, human) and in domestic fowls (e.g. chicken, duck).

For the treatment of *Escherichia coli* infection, for instance, a solution of 0.5–2.0 g of, for example, cefmenoxime and 0.5–10 g of the compound of the formula (I) in 10–100 ml of physiological saline is administered to human adults two to three times a day in admixture with an injectable solution for intravenous drip infusion.

The compound of the present invention is also a very promising intermediate for the synthesis of novel drugs.

When the compound of the present invention was intravenously administered to mice, the $LD_{50}$ was more than 1 g/kg.

The following examples illustrate the invention in more detail. However, they should by no means be construed as limiting the present invention. Unless otherwise stated, each percentage value is on 2 weight-/volume basis.

EXAMPLE 1

Two 2-liter Sakaguchi flasks each containing 500 ml of a medium containing 1% glucose, 0.5% Polypepton (Daigo Nutritive Chemicals, Ltd.), 0.5% meat extract and 0.5% sodium chloride (pH 7.0) were inoculated with cells of *Pseudomonas acidophila* G-6302 strain (FERM-P No. 4344; IFO 13774; ATCC 31363) grown on a slant nutrient agar and incubated at 28° C. with reciprocal shaking for 48 hours to give a seed culture.

A 200-liter stainless steel fermentor was charged with 120 liters of a medium containing 3% glycerol, 0.1% glucose, 0.5% Polypepton, 0.5% meat extract, 0.5% NaCl and 0.1% cysteine, and the medium was adjusted to pH 7.0 with 30% sodium hydroxide solution, then steam-sterilized at 120° C. for 20 minutes, and inoculated with the above seed culture. Incubation was carried out at a temperature of 28° C., a rate of aeration of 120 liters/minute and a rate of stirring of 180 rpm for 78 hours. The culture broth was centrifuged on a Sharpless centrifuge for separation of bacterial cells. There was obtained 110 liters of supernatant, which, after adjustment to pH 4.2, was passed through a column packed with 15 liters of activated carbon ("Shirasagi" for chromatographic use, Takeda Chemical Industries, Ltd.) for adsorption of the active substance. After washing with 45 liters of water, elution was conducted with 45 liters of 50 v/v % acetone-water. An aliquot of each 10-liter eluate fraction was tested for the active substance using a bouillon agar medium containing 0.05 $\mu$g/ml of cefmenoxime with *Escherichia coli* IFO 12734 as the test organism. As a result, fractions Nos. 2 and 3 were pooled and, after addition of 20 liters of water, passed through a column packed with 10 liters of Dowex-1 (Cl) (Dow Chemical, USA). After washing with 25 liters of water, elution was carried out with 50 liters of 5% sodium chloride solution in water. The active fractions were pooled and, after adjustment to pH 4.0, passed through a column packed with activated carbon (8 liters). After washing with 24 liters of water, elution was performed with 20 v/v % methanol-water. The active fractions were collected and concentrated under reduced pressure to 50 ml, 200 ml of acetone was added, and the resulting precipitate was collected by filtration, washed with 50 ml of acetone and 100 ml of ether and dried under reduced pressure to give 25 g of crude F2.

In 500 ml of M/25 phosphate buffer (pH 6.6) was dissolved 10 g of the crude F2 and the solution was passed through a 200-ml column of QAE Sephadex A-25 (Pharmacia, Sweden) buffered with the same buffer as above, for adsorption of F2. The column was washed with 400 ml of the same buffer and then with 400 ml of the same buffer with 0.5% of sodium chloride added thereto. Thereafter, elution was carried out with the same buffer with 1% of sodium chloride added thereto. The active fractions were pooled and, after adjustment to pH 3.0 with 1N hydrochloric acid, passed through a 60-ml column of activated carbon. The column was washed with 200 ml of water and then with 100 ml of 50 v/v % methanol-water. Elution was carried out with 8.0 v/v % isobutanol-water. The active eluate fractions were pooled and, after adjustment to pH 5.5, concentrated under reduced pressure. The concentrate was dissolved by addition of 50 ml of methanol, and the solution was filtered and allowed to stand in a cool place. The resulting crystalline precipitate was filtered off, washed with ether and dried over phosphorus pentoxide at 40° C. under reduced pressure for 6 hours. There was thus obtained 2.8 g of the monosodium salt of F2 as crystals. Its infrared absorption spectrum is shown in FIG. 1.

Elemental analysis: C, 32.11; H, 5.38; N, 7.27; S, 10.67; Na, 3.8%

EXAMPLE 2

In 90 ml of water was dissolved 3.0 g of the monosodium salt of F2 obtained in Example 1. After 4.5 ml of 1N sodium hydroxide was added thereto under cooling, the solution was carefully adjusted to pH 7.0 with 1N sodium hydroxide while measuring the pH and then was lyophilized to give 3.1 g of the disodium salt of F2 as a white powder. An infrared absorption spectrum for this product after drying at 40° C. under reduced pressure for 6 hours in shown in FIG. 2. Elemental analysis gave the following results: C, 31.35; H, 5.24; N, 6.78; S, 10.38; Na 7.1%.

EXAMPLE 3

Two 2-liter Sakaguchi flasks each containing 500 ml of a medium containing 1% glucose, 0.5% Polypepton (Daigo Nutritive Chemicals, Ltd.), 0.5% meat extract and 0.5% sodium chloride (pH 7.0) were inoculated with cells of *Pseudomonas mesoacidophila* SB-72310 (FERM-P No. 4653; IFO 13884; ATCC 31433) grown on a slant nutrient agar and incubated at 28° C. with reciprocal shaking for 48 hours to give a seed culture.

A 200-liter stainless steel fermentor was charged with 120 liters of a medium containing 3% glycerol, 0.1% glucose, 0.5% Polypepton, 0.5 meat extract, 0.5% NaCl and 0.1% cysteine, and the medium was adjusted to pH 7.0 with 30% sodium hydroxide solution, then steam-sterilized at 120° C. for 20 minutes and inoculated with the above seed culture. Incubation was then carried out at a temperature of 28° C., a rate of aeration of 120 liters per minute and a rate of stirring of 180 rpm for 78 hours. The culture broth was centrifuged on a Sharpless centrifuge for separation of bacterial cells. There was obtained 110 liters of supernatant, which, after adjustment to pH 4.2, was passed through a column packed with 15 liters of activated carbon ("Shirasagi" for chromatography, Takeda Chemical In Industries, Ltd.) for adsorption of the active substance. After washing with 45 liters of water, elution was performed with 45 liters of 50 v/v % acetone-water. An aliquot of each 10-liter eluate fraction was tested for the active substance using a bouillon agar medium containing 0.05 μg/ml of cefmenoxime with *Escherichia coli* IFO 12734 as the test organism. Fractions Nos. 2 and 3 were pooled and, after addition of 20 liters of water, passed through a column packed with 10 liters of Dowex-1 (Cl) (Dow Chemical, USA). After washing with 25 liters of water, elution was performed with 50 liters of 5% sodium chloride solution in water. The active fractions were pooled, adjusted to pH 4.0 and again passed through an activated carbon column (8 liters). Following washing with 24 liters of water, elution was performed with 20 v/v % methanol-water. The active fractions were pooled and concentrated to 50 ml under reduced pressure, 200 ml of acetone was added, and the resulting precipitate was collected by filtration, washed with 50 ml of acetone and 100 ml of ether and dried under reduced pressure. There was obtained 21 g of crude product.

In 500 ml of M/100 phosphate buffer (pH 6.6) was dissolved 10 g of the crude product and the solution was passed through a 200-ml column of QAE Sephadex A-25 (Pharmacia, Sweden) buffered with the same buffer as above, for adsorption of F2. The column was washed with 400 ml of the same buffer and then with 400 ml of the same buffer with 0.5% of sodium chloride added thereto. Then, elution was performed with the same buffer with 1% of sodium chloride added thereto. The active fractions were pooled, adjusted, to pH 3.0 with 1N hydrochloric acid and passed through a 60-ml column of activated carbon. The column was washed with 200 ml of water and elution was carried out with 8 v/v % isobutanol-water. The active fractions were pooled, adjusted to pH 5.5 and concentrated under reduced pressure. The concentrate was dissolved by addition of 50 ml of methanol and the solution was allowed to stand in a cool place. The resulting crystalline precipitates were collected by filtration, washed with ether and dried over phosphorus pentoxide at 40° C. under reduced pressure for 6 hours. There was obtained 1.5 g of the monosodium salt of F2 as crystals. Its infrared absorption spectrum is shown in FIG. 3. Elemental analysis: C, 32.59; H, 5.22; N, 6.93; S, 10.14; Na, 3.7%.

EXAMPLE 4

In 30 ml of water was dissolved 1.0 g of the monosodium salt of F2 as obtained in Example 3. Following addition of about 1.5 ml of 1N sodium hydroxide under cooling, the solution was carefully adjusted to pH 7.0 while measuring the pH. The thus-neutralized solution was lyophilized to give 1.05 g of the disodium salt of F2 as white powder. An infrared spectrum of this product after drying at 40° C. for 6 hours is shown in FIG. 4. Elemental analysis gave the following data: C, 30.83; H, 5.35; N, 6.91; S, 9.68; Na, 7.3%.

EXAMPLE 5

Cells of *Pseudomonas mesoacidophila* SB-72310 (FERM-P No. 4653; IFO 13884; ATCC-31433) were inoculated into two 2-liter Sakaguchi flasks each containing 500 ml of a medium composed of 1% glucose, 0.5% Polypepton (Daigo Eiyo Chemical Co., Ltd.), 0.5% meat extract and 0.5% sodium chloride (pH 7.0) and the inoculated flasks were incubated on a reciprocating shaker at 28° C. for 48 hours to prepare a seed inoculum.

Then a 200-liter stainless steel fermentor was charged with 120 l of a medium composed of 3% glycerol, 0.1% glucose, 0.5% Polypepton, 0.5% meat extract, 0.5% NaCl and 0.1% cysteine, the pH of which was adjusted to pH 7 with 30% sodium hydroxide. The fermentor was steam-sterilized at 120° C. for 20 minutes, after which the medium was inoculated with the seed inoculum. Cultivation was conducted at 28° C. with 120 l/min. aeration and at 180 r.p.m. for 78 hours. The culture broth was centrifuged with a Sharpless centrifuge to separate the cells to recover 110 l of a supernatant. It was adjusted to pH 4.2 and passed through a column of 15 l activated carbon (Chromatography grade Shirasagi, Takeda Chemical Industries, Ltd.) to adsorb the active compounds. The column was rinsed with 45 l of water and elution was carried out with 45 l of 50 v/v % aqueous acetone. The eluate was collected in 10 l fractions and the active fractions were detected using plates of broth agar containing 0.05 g/ml of cefmenoxime and, as the test organism, *Escherichia coli* IFO 12734. Fraction Nos. 2 and 3 were pooled, diluted with 20 l of water and passed through a column of 10 l Dowex-1(Cl) (Dow and Chemical, U.S.A.). After the column was rinsed with 24 l of water, elution was carried out with 20 v/v % aqueous methanol. The active fraction was concentrated under reduced pressure to 50 ml, followed by addition of 200 ml of acetone. The resultant precipitate was recovered by filtration, washed with 50 ml of acetone and 100 ml of ether, and dried in vacuo to give 21 g of a crude product.

Ten (10) grams of this crude product was dissolved in 500 ml of 1/100 M-phosphate buffer (pH 6.6) and passed through a column of 200 ml QAE-Sephadex A-25 buffered with the same buffer as above. The column was washed with 100 ml of the same buffer as above and eluation was carried out with 2000 ml of the same buffer containing 0.5% of sodium chloride. The fractions showing F3 activity were pooled, adjusted to pH 3.0 with 1N-HCl, and passed through a column of 40 ml activated carbon. The column was rinsed with 200 ml of water and elution was carried out with 50 v/v % aqueous methanol. The active fractions were pooled, concentrated under reduced pressure and lyophilized. The white powder thus obtained was dried over phosphorus pentoxide under reduced pressure at 40° C. for 6 hours to give 0.85 g of a powder (sodium salt of F3). The infrared absorption spectrum (KBr) of this powder is shown in FIG. 5.

Elemental analysis: C, 32.08; H, 5.33; N, 5.17; S, 6.28; Na, 4.60%

EXAMPLE 6

Cells of *Pseudomonas acidophila* G-6302 (FERM-P No. 4344; IFO 13774; ATCC-31363) grown on a nutrient broth agar slant were used to inoculate two 2-liter Sakaguchi flasks each containing 500 ml of a medium composed of 1% glucose, 0.5% Polypepton, 0.5% meat extract and 0.5% sodium chloride (pH 7.0) and the inoculated medium was incubated on a reciprocating shaker at 28° C. for 48 hours to give a seed inoculum.

Separately, a 200-liter stainless steel fermentor was charged with 120 l of a medium composed of 3% glycerol, 0.1% glucose, 0.5% Polypepton, 0.5% meat extract, 0.5% NaCl and 0.1% cysteine and after adjustment to pH 7.0 with 30% sodium hydroxide was steam-sterilized at 120° C. for 20 minutes. The fermentor was then inoculated with the above seed inoculum and incubation was carried out at 28° C. and 180 r.p.m. with 120 l/min. aeration for 78 hours. The resulting broth was centrifuged with a Sharpless centrifuge to separate the cells and give 110 l of a supernatant. This supernatant was adjusted to pH 4.2 and passed through 15 l of activated carbon (Chromatography grade Shirasagi, Takeda Chemical Industries, Ltd.). After an aqueous rinse with 45 l of water, elution was carried out with 45 l of 50 v/v % aqueous acetone. The eluate was collected in 10-liter fractions which were assayed for activity using plates of broth-agar containing 0.05 μg/ml of cefmenoxime and, as the test organism, *Escherichia coli* IFO 12734. Fraction Nos. 2 and 3 were pooled, diluted with 20 l of water and passed through a column of 10 l Dowex-1(Cl) (Dow and Chemical, U.S.A.). The column was rinsed with 25 l of water and elution was performed with 50 l of 5% aqueous sodium chloride. The active fractions were pooled, adjusted to pH 4.0 and passed again through a column (8 l) packed with activated carbon. After the column was rinsed with 24 l of water, elution was carried out with 20 v/v % aqueous methanol. The active fractions were pooled and concentrated under reduced pressure to 50 ml. To the residue was added 200 ml of acetone and the resultant precipitate was recovered by filtration, washed with 50 ml of acetone and 100 ml of ether, and dried in vacuo to give 25 g of a crude product.

A 10 g portion of the crude product was dissolved in 500 ml of M/100 phosphate buffer (pH 6.6) and the solution was poured on a column of 200 ml QAE-Sephadex A-25 buffered with the same buffer as above to have the product adsorbed thereon. The column was washed with 1000 ml of the same buffer as above and elution was carried out with 2000 ml of the same buffer containing 0.5% of sodium chloride. Fractions containing F3 activity were pooled, adjusted to pH 3.0 with 1N-HCl, and passed through a column of activated carbon. The column was rinsed with 200 ml of water and elution was carried out with 50 v/v % aqueous methanol. The active fractions were pooled, concentrated under reduced pressure, and lyophilized. The resulting white powder was dried in vacuo over phosphorus pentoxide at 40° C. for 6 hours to give 1.3 g of a powder (Sodium salt of F3).

Elemental analysis: C, 32.28; H, 5.53; N, 5.18; S, 6.25; Na, 4.52%

EXAMPLE 7

Monosodium salt of F2 (5.9 g), which was obtained by the method of Example 1, was dissolved in 150 ml of 1N-hydrochloric acid-methanol, and then treated at 90° C. for 4 hours. After methanol was distilled out, the residue was dissolved in 100 ml of water and passed through a column (100 ml) of Amberlite IR-45(OH$^-$). The solution which passed through the column, together with washings, was again passed through a column (100 ml) of Amberlite IRC-50 (H$^+$). The solution which was thus passed the column, together with washings, was diluted to 500 ml with water, and then passed through a column (100 ml) of Amberlite IRA-68 (OH$^-$). The column was washed with 100 ml of water, elution was carried out with 1N-aqueous acetic acid. The eluate, together with washings, was concentrated. The residue was dissolved in 10 ml of water, and the solutions was subjected to a column chromatography of Sephadex LH-20 (3.3×50 cm). Elution was carried out with 10% methanol-water, fractions of 210 to 230 ml were pooled and concentrated under reduced pressure, and lyophilized. The resulting powder (1.0 g) was treated with ethanol. Thus, 0.78 g of F4 was obtained as crystaline solid.

Specific rotation: $[\alpha]_D^{23} + 1.4°$ (c=1.0, N-CH$_3$COOH)

Elemental analysis, for $C_{16}H_{29}N_3O_{11}S \cdot H_2O$: Calcd. (%): C, 39.25; H, 6.38; N, 8.59; S, 6.55. Found (%): C, 38.91; H, 6.42; N, 8.47; S, 6.16.

Infrared absorption spectrum: An absorption spectrum as obtained by the potassium bromide disc method is shown in FIG. 6.

Amino acid analysis (hydrolysis with 6N-HCl at 110° C. for 8 hours): D-glucosamine, 0.92; taurine, 1.00; 4-hydroxy-5-hydroxymethylproline, 0.85 (average recovery 85%).

EXAMPLE 8

Sodium salt of F3 (70 mg), which was obtained by the method of Example 5, was dissolved in 17 ml of 0.2N-hydrochloric acid, and then was allowed to stand at 90° C. for 2 hours. The solution was neutralized with 3.4 ml of 1N-sodium hydroxide, and passed through a column (50 ml) of activated carbon. The column was washed with 150 ml of water, and then elution was carried out with 8% aqueous iso-butanol. The fractions of 100 to 250 ml were pooled and concentrated under reduced pressure, the obtained residue was dissolved in a small amount of water. The solution was subjected to a column chromatography of 50 ml QAE-Sephadex A-25 buffered with 0.05M-phosphate buffer (pH 6.1). Elution was carried out with the same buffer as above, the fractions of 19 to 54 ml were pooled and the solution was passed through a column (20 ml) of activated carbon. The column was washed with 60 ml of water, and the elution was carried out with 8% aqueous iso-butanol. The fractions of 40 to 70 ml were pooled, and iso-butanol was ditilled out, the residue was lyophilized. Thus, 28 mg of F5 was obtained as white powders.

Elemental analysis, for $C_{14}H_{24}O_9N_2 \cdot H_2O$: Calcd. (%): C, 43.97; H, 6.85; N, 7.32. Found (%): C, 44.05; H, 6.93; N, 7.10.

Infrared absorption spectrum: An absorption spectrum as obtained by the pottasium bromide disc method is shown in FIG. 7.

TLC Rf: The Rf values on the silica gel plate (Merck, 60F 254)

Rf=0.14 (n-propanol:water=4:1)

Rf=0.22 (n-propanol:acetic acid:water=2:1:1)

Amino acid analysis (hydrosis with 6N-HCl at 110° C. for 14 hours): Glucosamine, 1.00; 4-hydroxy-5-hydroxymethyl proline, 0.93 (average recovery 82%).

Figure 1:
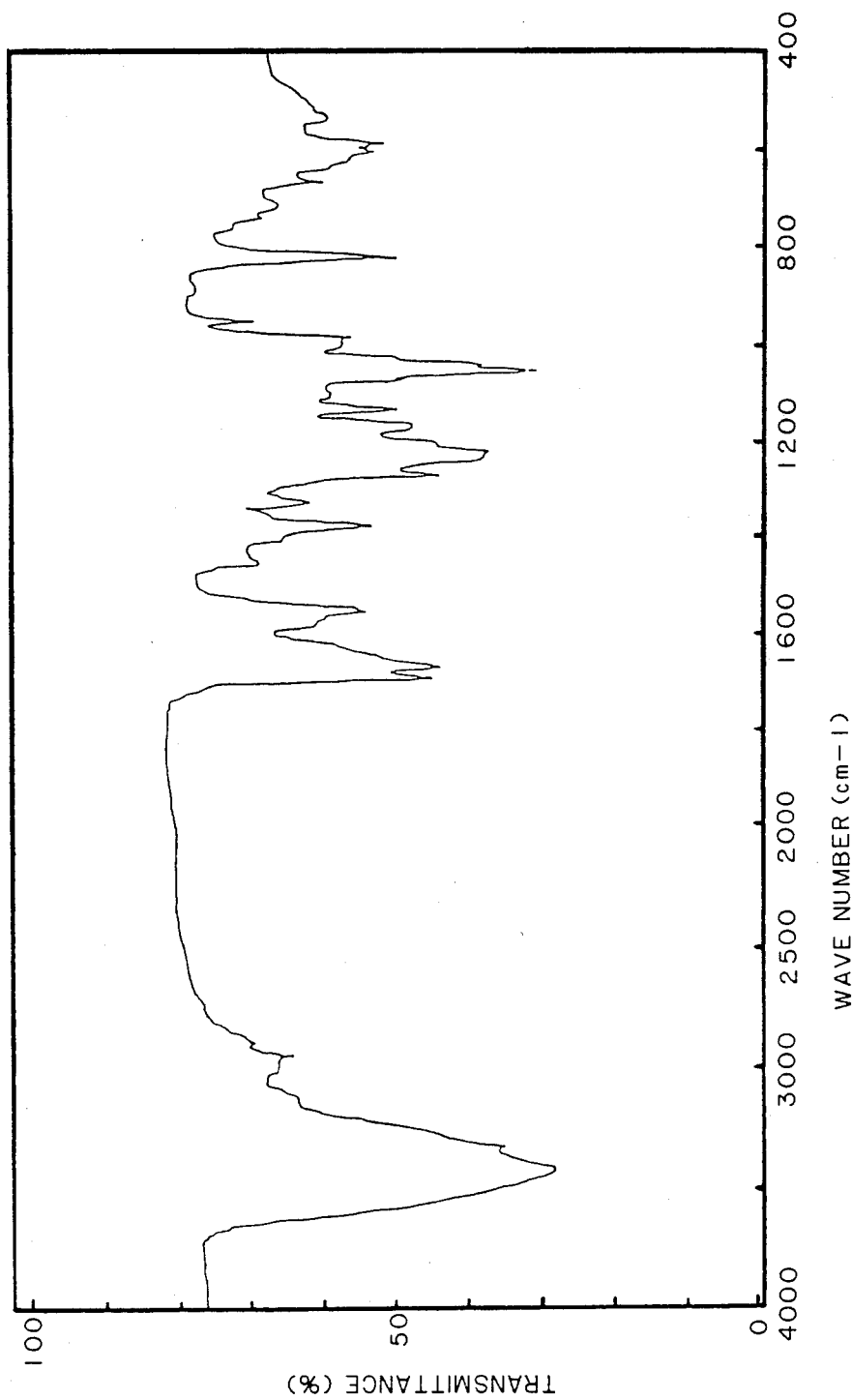
FIGS. 1, 2, 3, 4, 5, 6 and 7 show infrared absorption spectra of the monosodium salt of F2 as obtained in Example 1, the disodium salt of F2 as obtained in Example 2, the monosodium salt of F2 as obtained in Example 3, the disodium salt of F2 as obtained in Example 4, the sodium salt of F3 as obtained in Example 5, the F4 as obtained in Example 7 and the F5 as obtained in Example 8, respectively.
Figure 2:
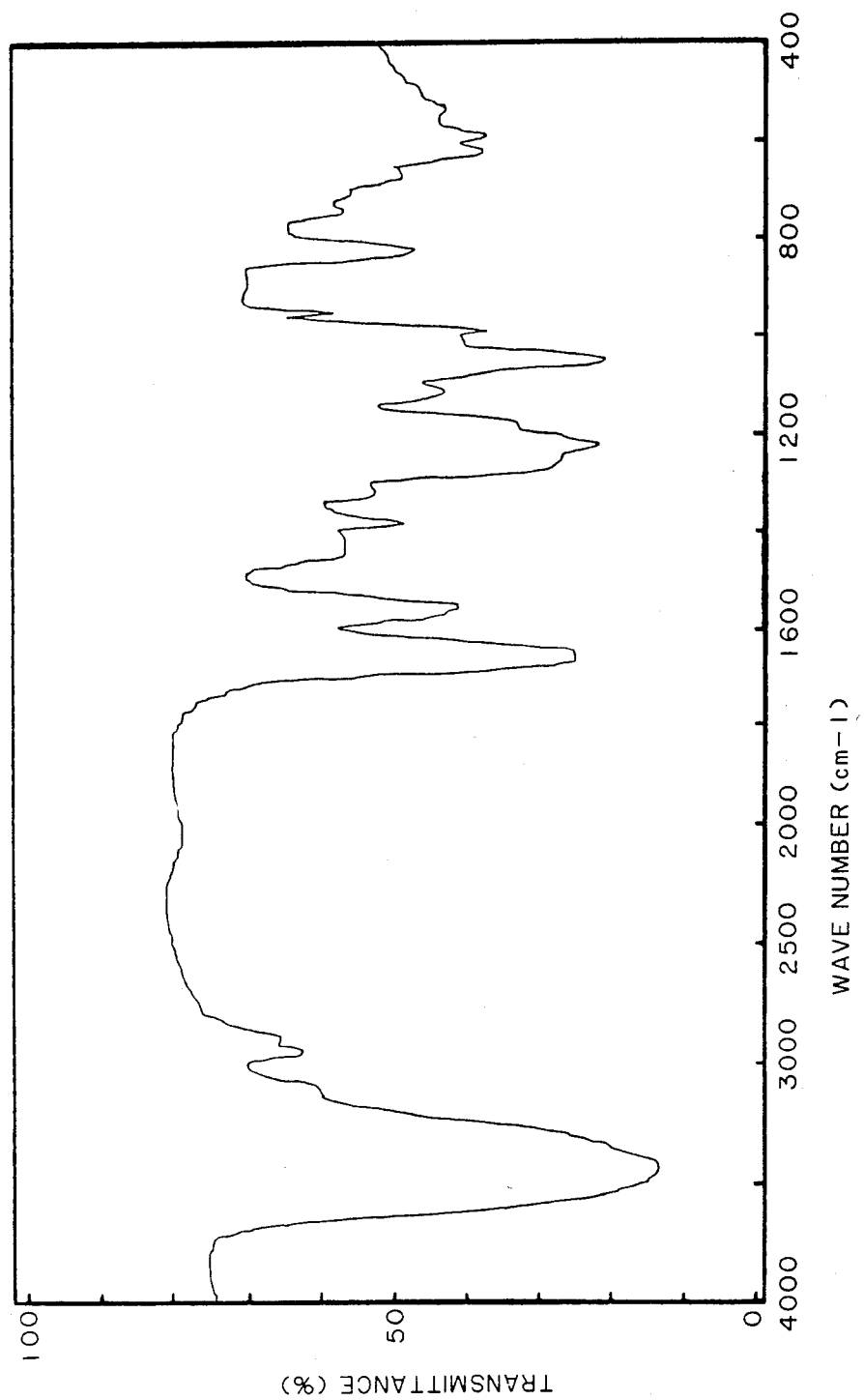
Figure 3:
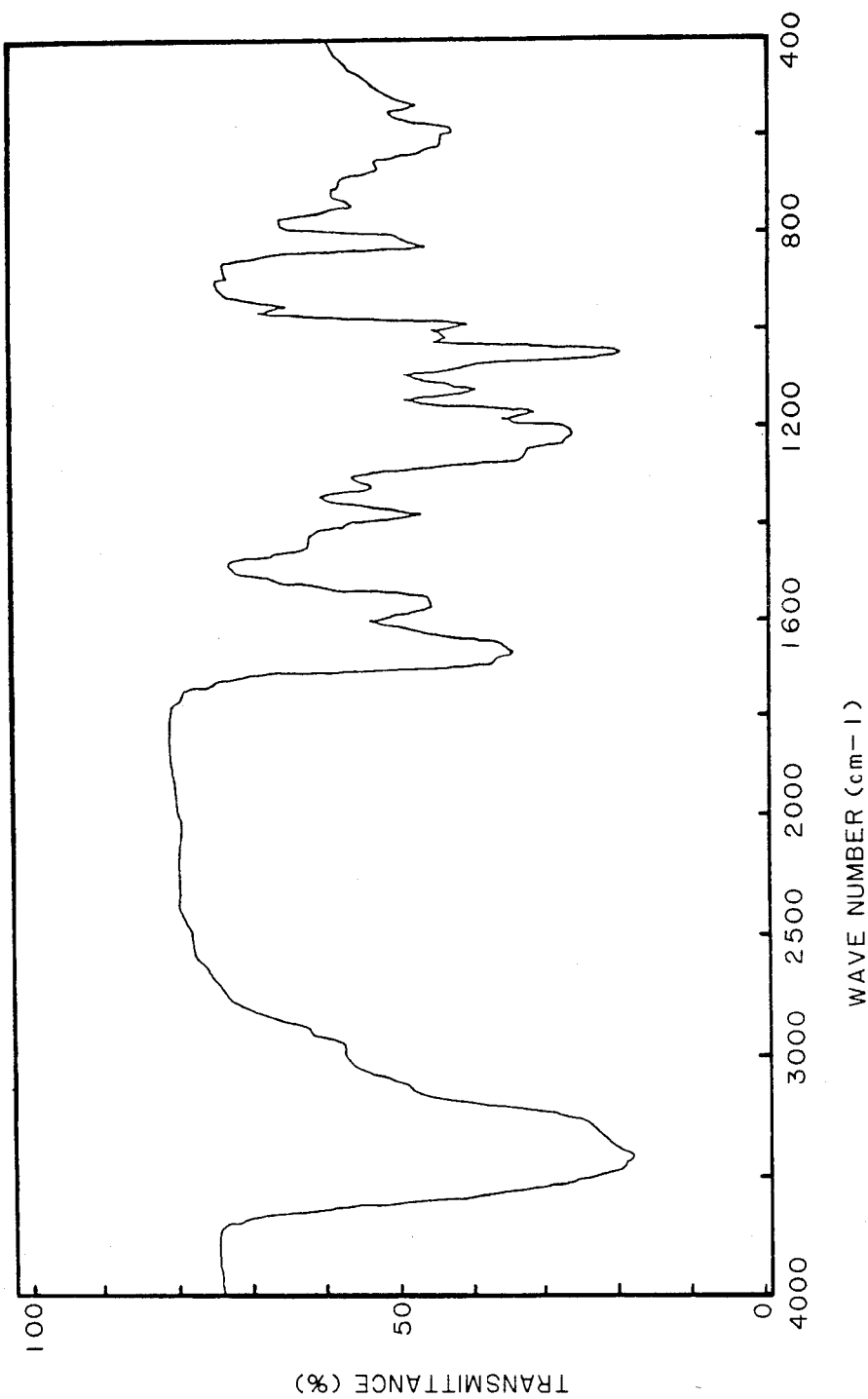
Figure 4:
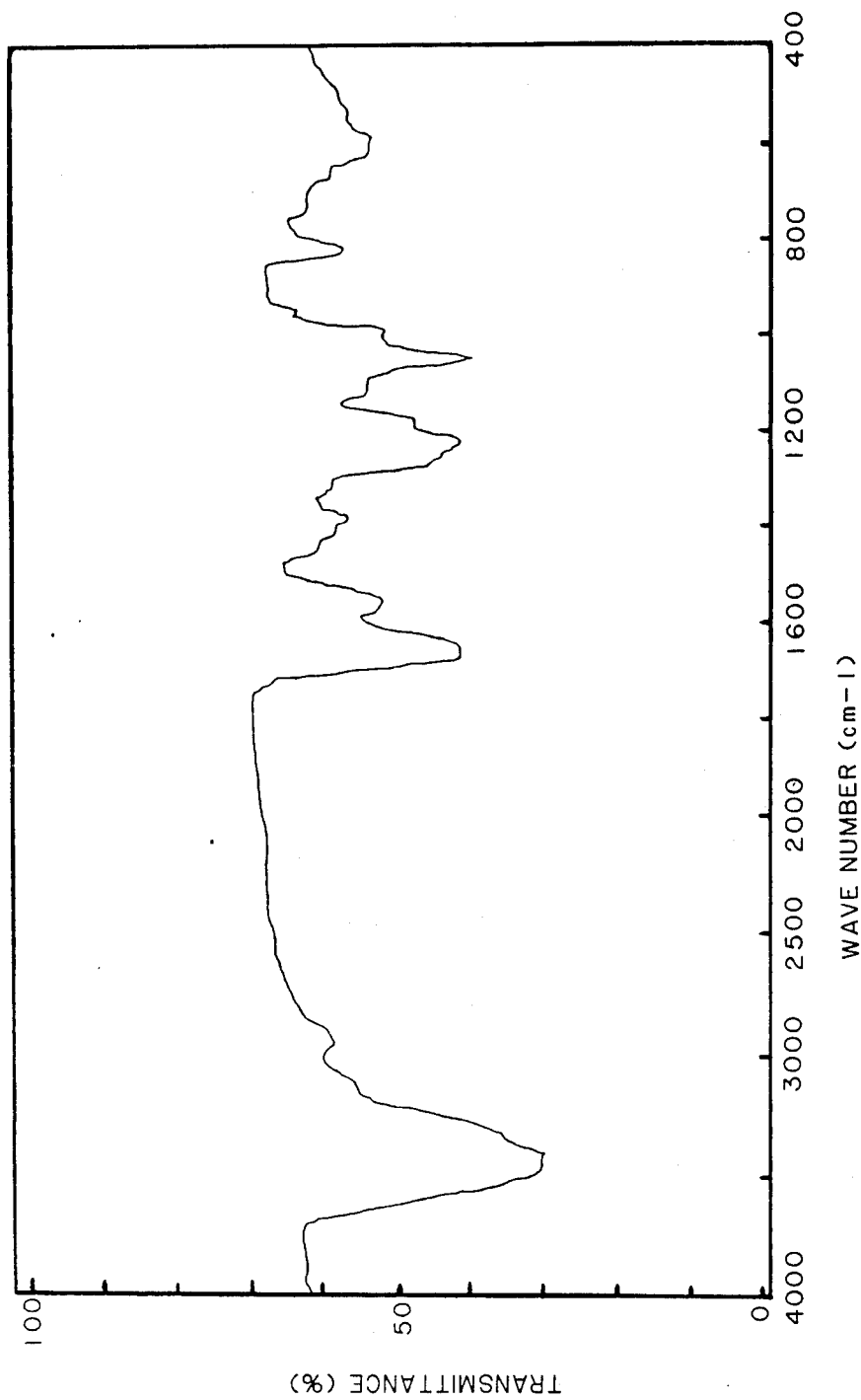
Figure 5:
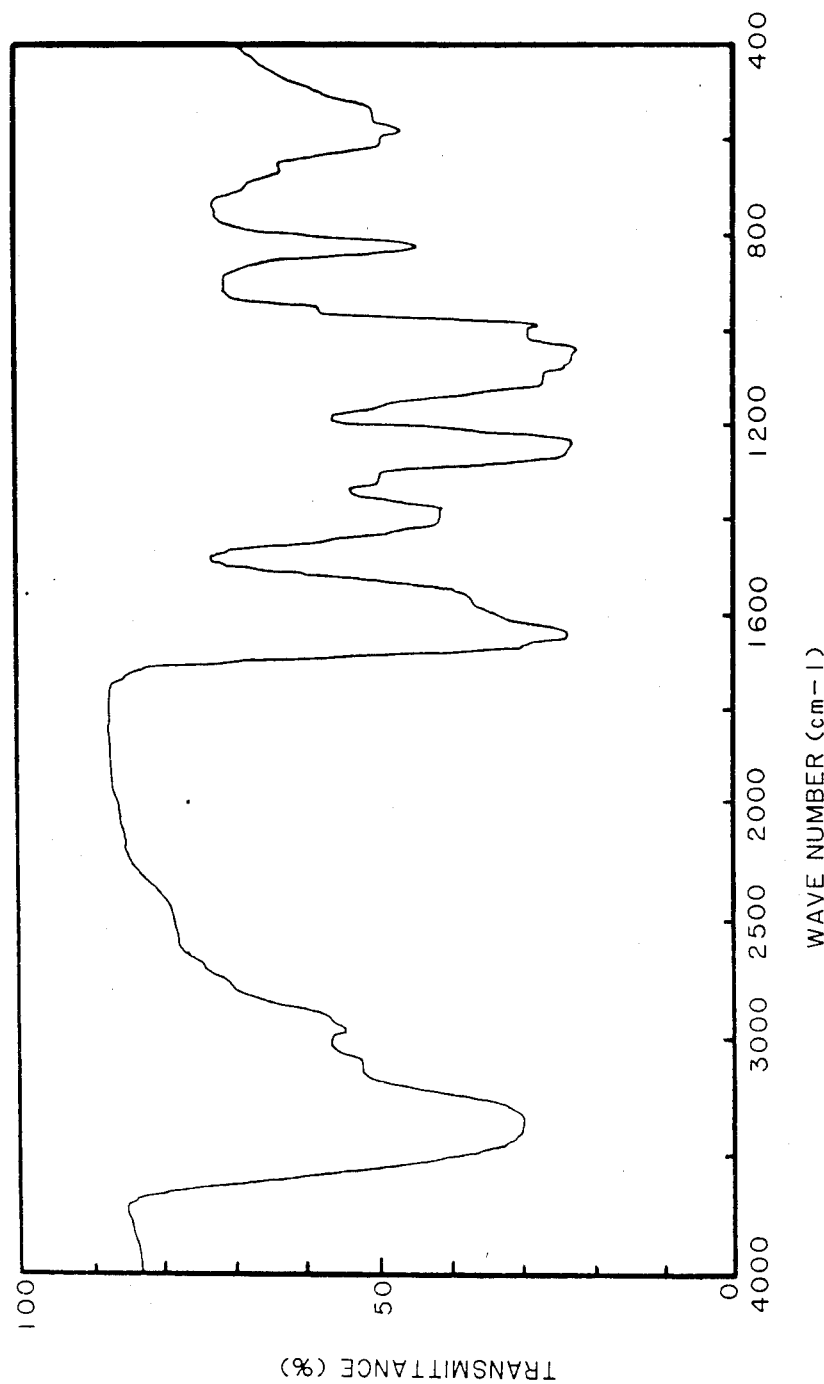
Figure 6:
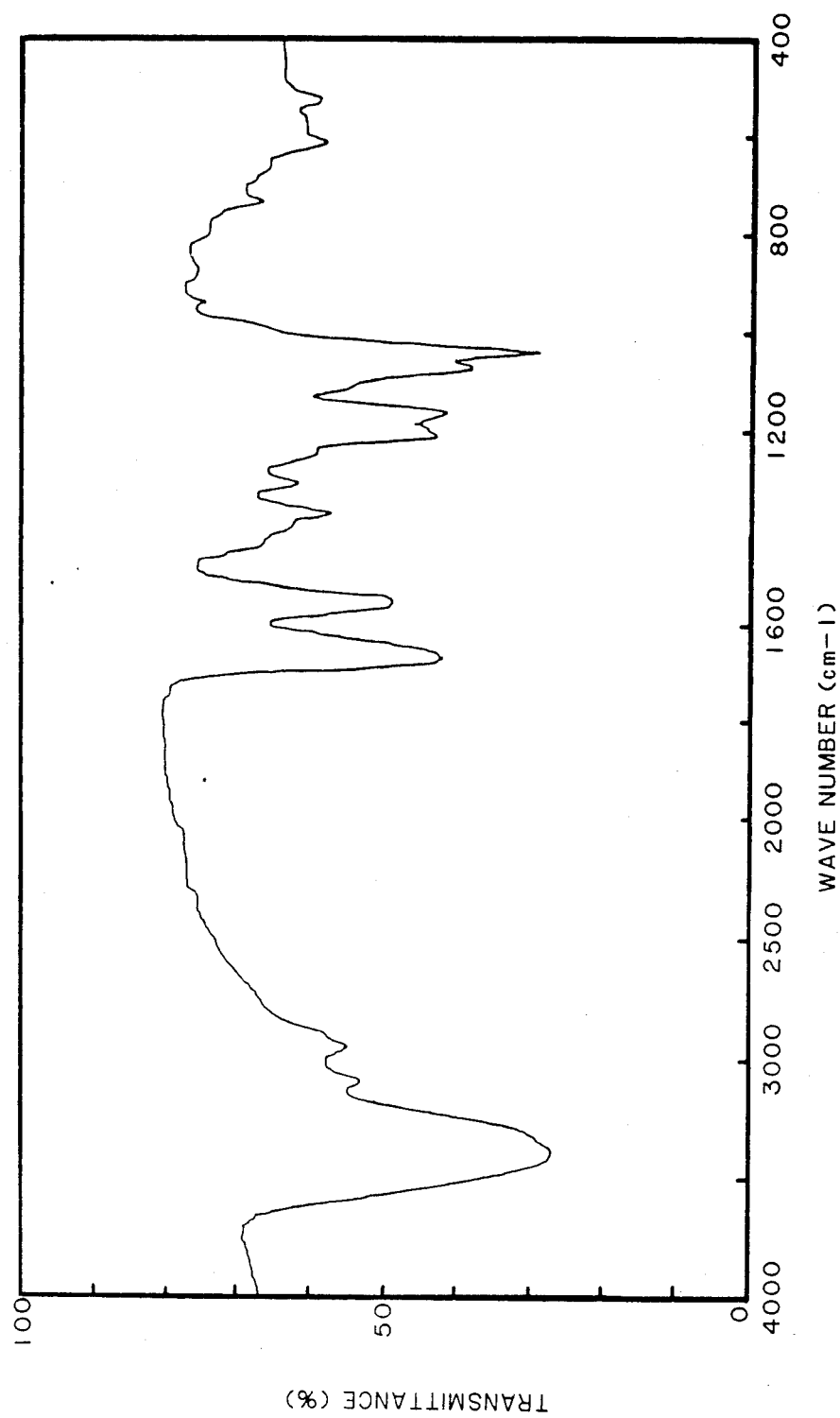
Figure 7:
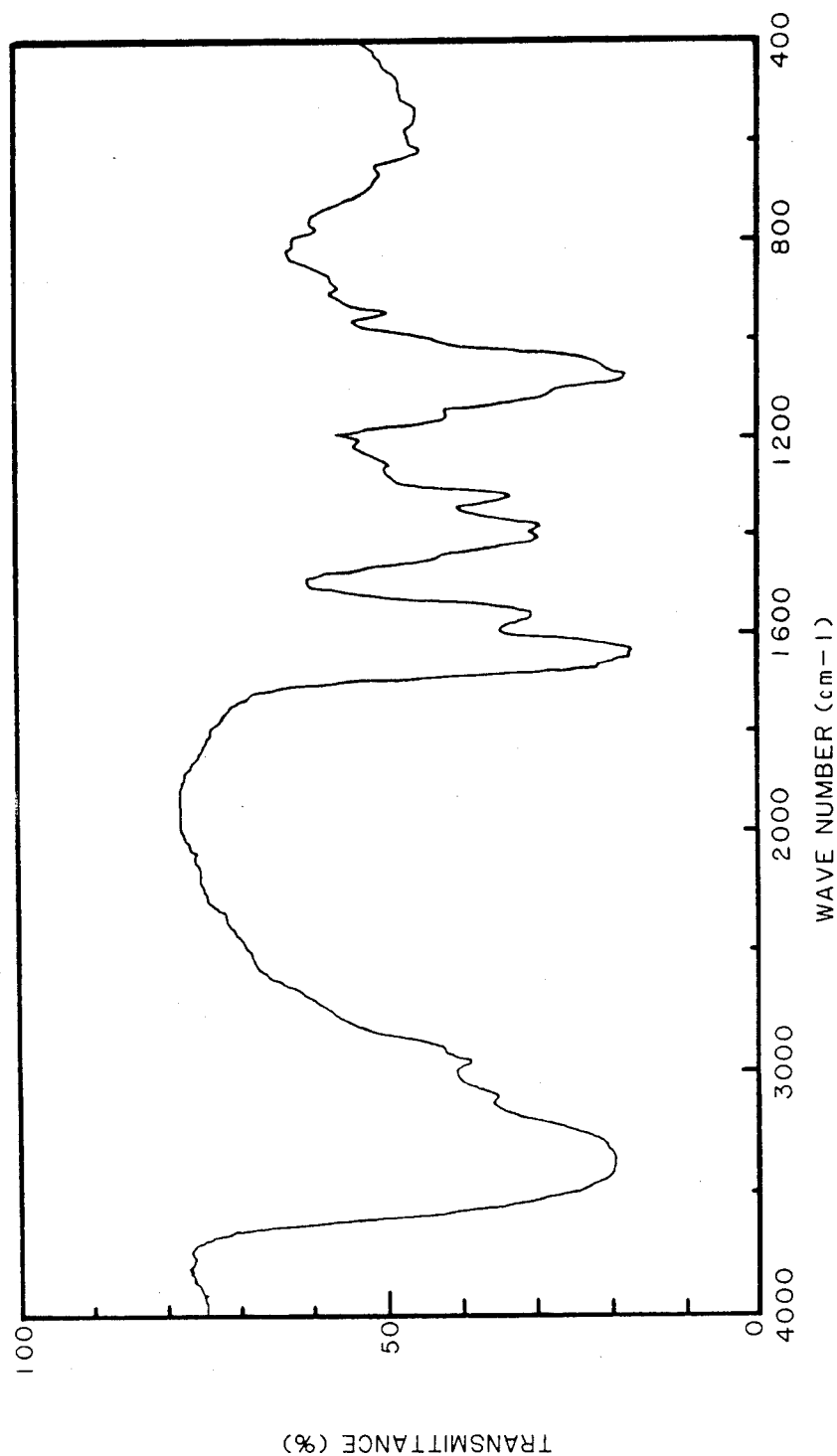

What we claim is:

1. A compound of the formula:

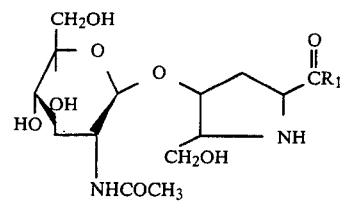

wherein $R_1$ is $NHCH_2CH_2SO_3H$ or OH, or a pharmaceutically acceptable salt thereof.

2. A substantially pure compound of the formula:

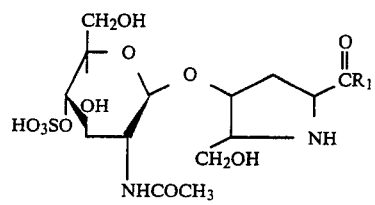

wherein $R_1$ is $NHCH_2CH_2SO_3H$ or OH, or a pharmaceutically acceptable salt thereof.

* * * * *